United States Patent [19]

Fukaya et al.

[11] Patent Number: 4,849,429
[45] Date of Patent: Jul. 18, 1989

[54] CERTAIN 1,4-DIHYDRO-2,6-DILOWER-ALKYL-4-(MONO-SUBSTITUTED PYRIDYL) USEFUL FOR TREATING CORONARY ARTERY OR CEREBRAL ARTERY DISEASE

[75] Inventors: Chikara Fukaya, Osaka; Atsuyuki Ashimori, Yawata; Taizo Ono, Kyoto; Kazumasa Yokoyama, Toyonaka, all of Japan

[73] Assignee: The Green Cross Corporation, Osaka, Japan

[21] Appl. No.: 906,268

[22] Filed: Sep. 9, 1986

[30] Foreign Application Priority Data

Sep. 13, 1985 [JP] Japan .................................. 60-203935
Nov. 22, 1985 [JP] Japan .................................. 60-263093
May 14, 1986 [JP] Japan .................................. 61-111560

[51] Int. Cl.$^4$ .................. C07D 211/90; C07D 401/04; A61K 31/455
[52] U.S. Cl. ...................... 514/307; 514/314; 514/332; 514/333; 546/147; 546/174; 546/257; 546/258; 546/321
[58] Field of Search ............... 546/257, 258, 321, 322, 546/147, 174; 514/332, 307, 314, 333

[56] References Cited

U.S. PATENT DOCUMENTS

| 3,485,847 | 12/1969 | Bossert et al. ........................ | 546/321 |
| 3,644,627 | 2/1972 | Bossert et al. ........................ | 514/356 |
| 3,985,758 | 10/1976 | Murakami et al. .................... | 546/321 |
| 4,618,607 | 10/1986 | Araki et al. ........................... | 514/212 |

FOREIGN PATENT DOCUMENTS 0174653 3/1986 European Pat. Off. ............ 546/194
2218644 10/1973 Fed. Rep. of Germany ...... 546/258

OTHER PUBLICATIONS

Chem. Abstracts, vol. 80 (1), Abst. No. 14958g, Jan. 7, 1974.
Chem. Abstracts, vol. 96 (23), Abst. No. 96:199, 719b, Jun. 7, 1982.
The Merck Index, 10th Ed., pp. 6368, 6335.

Primary Examiner—Alan L. Rotman
Attorney, Agent, or Firm—Cushman, Darby & Cushman

[57] ABSTRACT

There is provided a dihydropyridine derivative having the formula

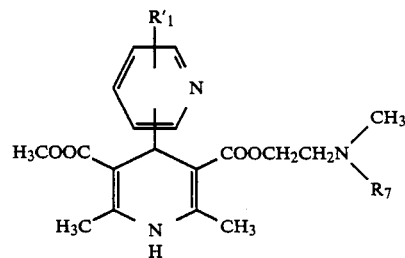

wherein $R'_1$ denotes methyl, chlorine, bromine, fluorine, trifluoromethyl, nitro, cyano or methoxy, $R_7$ denotes benzyl; and the dihydropyridine links to the 2-, 3-, or 4-position of the pyridine.

The compound has an activity as a Ca-antagonist, and is useful for treating vascular disorders such as coronary artery disease, celebral artery disease, hypertension and the like.

23 Claims, No Drawings

CERTAIN 1,4-DIHYDRO-2,6-DILOWER-ALKYL-4-(MONO-SUBSTITUTED PYRIDYL) USEFUL FOR TREATING CORONARY ARTERY OR CEREBRAL ARTERY DISEASE

This invention relates to a novel 4-pyridyldihydropyridine derivative. More particularly, it is concerned with a 4-pyridyl-dihydropyridine derivative having an activity such as calcium-antagonism, blood pressure lowering and phosphodiesterase inhibition.

Hitherto, a 4-phenyl-dihydropyridine-3,5-dicarboxylic acid ester has been known as having such activity (U.S. Pat. No. 3,644,627). For Example, 2,6-dimethyl-4-(2-nitrophenyl)-1,4-dihydropyridine-3,5-dicarboxylic acid dimethyl ester has been on market as being called Nifedipine (The Merck Index, 10th Edition). In view of improving water solubility of the dimethyl ester compound, an improvement was made by changing at least one of the ester moieties to an N-substituted aminoalkyl ester (U.S. Pat. No. 3,985,758), among which 2,6-dimethyl-4-(3-nitrophenyl)-1,4-dihydropyridine-3,5-dicarboxylic acid 3-$\beta$-(N-benzyl-N-methylamino)ethyl ester 5-methyl ester is described as being called Nicardipine in the Merck Index.

Although it is already known that these compounds are useful as an antihypertensive agent, vasodilator for peripheral and celebral blood vessels, and curative for coronary artery disorders (angina pectoris) relying on the above-mentioned activity, emergence of a dihydropyridine derivative having a more excellent effect is eagerly awaited.

An object of this invention is to provide a dihydropyridine derivative and the innoxious salt thereof, which have a more excellent pharmacological activity.

Another object of this invention is to provide a pharmaceutical composition comprising a dihydropyridine derivative having an excellent pharmacological activity.

This invention provides a novel dihydropyridine derivative (I) represented by the general formula

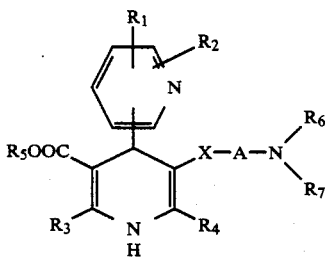

wherein $R_1$ and $R_2$ are the same as or different from each other and denote each hydrogen, provided that they cannot be hydrogen at the same time, or a nitro, cyano, halogen, alkyl, halogenated alkyl, alkoxy, halogenated alkoxy, alkylmercapto, alkylsulfinyl or alkylsulfonyl; $R_3$, $R_4$ and $R_5$ denote independently an alkyl; $R_6$ and $R_7$ independently denote hydrogen or alkyl or aralkyl which may be optionally substituted with halogen, or form a heterocyclic ring jointly with the adjacent nitrogen atom; X denotes a group —COO—; and A denotes an alkylene group; and an innoxious salt thereof. The present compounds have such an excellent Ca-antagonistic activity, antihypertensive effect, thrombocyte agglutination inhibition effect and phosphodiesterase inhibition effect and are useful as a medicine, for example as a coronary vessel vasodilator, celebral blood flow increasing agent, antihypertensive agent, preventive or curative agent for thrombosis, and phosphodiesterase inhibitor. Also, this invention provides a pharmaceutical composition comprising at least one member selected from the group consisting of the said dihydropyridine derivatives (I) and the innoxious salts thereof.

The dihydropyridine derivative (I) of this invention has a unique structure as compared with the prior dihydropyridine compounds known in the art and hence has a unique activity originating from the structure. Thus, it is expected that the dihydropyridine derivative (I) of this invention has a high organ and tissue selectivity, particularly in vasodilating action, and hence can attain an excellent pharmacological effect at a relatively small dose. As a result, it is characterized by its reduced systemic side effects.

In the present specification, halogen or halogenated means fluorine, chlorine, bromine and iodine, or their substituent. Preferably, it is fluorine, chlorine, and bromine, and preferably fluorine and bromine for $R_1$ and $R_2$. Alkyl may be either of straight chain or branched chain and includes, for example, alkyls of 1 to 6 carbon atoms such as methyl, ethyl, propyl, isopropyl, butyl, tert-butyl, pentyl and hexyl and preferably methyl for $R_3$, $R_4$, and $R_5$. Aralkyl groups include phenyl $C_1$-$C_3$ alkyl group, for example, benzyl, phenethyl, 1-phenylethyl, 3-phenylpropyl, 2-phenylpropyl and 1-phenylpropyl, the said phenyl groups being optionally substituted with substituents such as an alkyl and halogen, among which benzyl is preferred for $R_6$ or $R_7$. Alkylene groups have preferably 2 to 4 carbon atoms, may be either of straight chain or branched chain and include, for example, ethylene, trimethylene, propylene, tetramethylene, and 1,2-dimethylethylene group, and preferably ethylene group.

In the present specification, the alkyl moiety and halogen in the alkoxy, halogenated alkyl, alkylmercapto, alkylsulfinyl, and alkylsulfonyl group for $R_1$ or $R_2$ are the same as the above-defined alkyl and halogen. The halogenated alkyl may be those in which a part of their hydrogen atoms have been halogenated [$(CF_3)_2CHCH_2$—, $CF_3CH_2$— etc.] or those in which all of the hydrogen atoms have been halogenated (trifluoromethyl etc.), and trifluoromethyl is preferable for $R_1$ and $R_2$. Also, the halogenated alkoxy may be either those in which a part of their hydrogen atoms have been halogenated or those in which all of the hydrogen atoms have been halogenated.

In the general formula (I), the heterocyclic ring formed by $R_6$ and $R_7$ together with adjacent nitrogen atom may contain an additional hetero atom. Examples of such hetero atoms include an oxygen, a nitrogen and a sulfur atom. Examples of the heterocyclic ring include pyrrolidine, piperidine, morpholine, piperazine, 1,2,3,4-tetrahydroquinoline, 1,2,3,4-tetrahydroisoquinoline, imidazole, indole, isoindole, and benzimidazole. The heterocyclic ring may be optionally substituted by alkyl, aralkyl, halogen etc., which are the same as the above.

In the general formula (I), the position of pyridyl group to be connected at the 4-position of dihydropyridine is preferably the 2-, 3-, or 4-position thereof; and the position of the substituent $R_1$ or $R_2$, which are not hydrogen, may preferably be at a position next or next to one to the bond site of the pyridyl group with the dihydropyridyl group. Further, the relative position of the $R_1$ and the $R_2$ when the both present, is next, next to one or every third to each other.

The dihydropyridine derivative (I) can be piepared by reacting an optional part constituting the dihydropyridine derivative (I) with the remaining part of the derivative by a method known per se, particularly by subjecting them to dehydrating cyclization. For example, it can be prepared as follows.

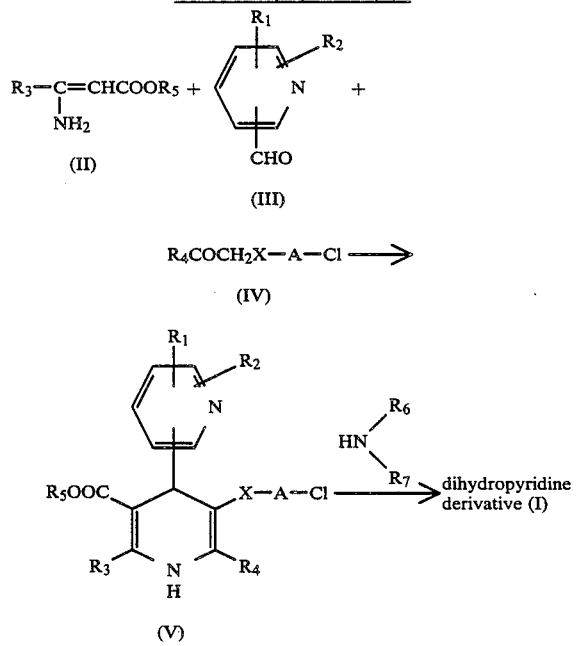

In the above formulas $R_1$, $R_2$, $R_3$, $R_4$, $R_5$, $R_6$, $R_7$, X and A are as defined above.

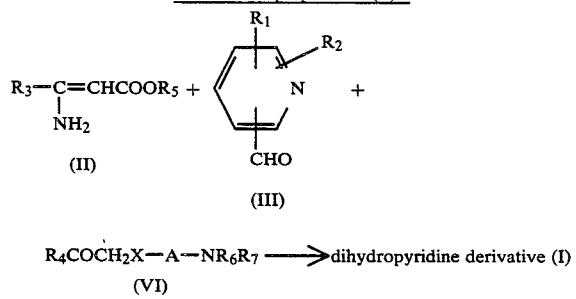

In the above formulas $R_1$, $R_2$, $R_3$, $R_4$, $R_5$, $R_6$, $R_7$, X and A are as defined above.

Each of the above-mentioned methods of preparation will be described in detail below.

Method of preparation (A)

In this method, the compounds (II), (III) and (IV) are first reacted in an appropriate solvent to prepare the compound (V). This reaction is carried out usually at about 30° C. to 150° C., preferably about 50° C. to 120° C., and particularly when the solvent used boils in the above-mentioned temperature range, at the boiling point. The solvent to be used is not particularly limited so long as it is inert to the reaction and includes, for example, alcohols such as methanol, ethanol, propanol, and isopropanol; ethers such as tetrahydrofuran, dioxane, and dimethoxyethane; N,N-dimethylformamide, dimethylsulfoxide, and acetonitrile. The reaction usually requires 1 to 20 hours for completion. As to the amount of the compounds (II), (III) and (IV) to be used, for 1 mole of any one of the three compounds 1 to 1.5 moles of each of the other two compounds is used. The starting compound (II) is already known or can be prepared by a known method [cf., for example,. J, Am. Chem. Soc., 67, 1017 (1945)]. The compound (IV) is already known or can be prepared by a known method [cf., for example, Chem. Pharm. Bull., 27 (6), 1426 (1979)]. The various substituted pyridine aldehyde (III) can be obtained by preparing the pyridine alcohol shown below by a known method and then oxidizing it with, for example, dimethylsulfoxide (DMSO)-dicyclohexylcarbodiimide (DCC)-phosphoric acid.

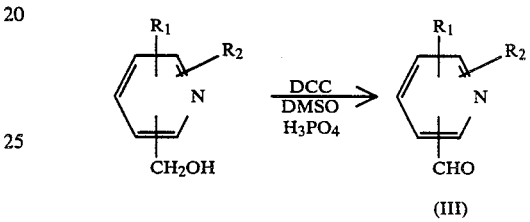

The compound (V) thus obtained is then treated with a secondary amine of the formula HN ($R_6$) ($R_7$) ($R_6$ and $R_7$ are the same as above) to give the dihydropyridine derivative (I). This reaction is carried out usually at about 50° C. to 130° C., preferably at about 70° C. to 110° C. Examples of preferred solvents to be used include toluene and N,N-dimethylformamide. The reaction is usually carried out by using 2 to 2.5 moles of the secondary amine relative to 1 mole of the compound (V). The reaction usually requires 1 to 20 hours for completion.

Method of preparation B

This method can be effected under substantially the same conditions as in the method A. The starting compound (VI) to be used in this method can be prepared by treating the starting compound (IV) used in the method A with the said secondary amine. Thus, it is easily prepared by dissolving the compound (IV) in a suitable solvent (for example, ethanol, dioxane, tetrahydrofuran, N,N-dimethylformamide), then adding to the solution the solution of about 2.5 equivalents of the secondary amine of the formula

and allowing the mixture to react at about 30° C. to 110° C. for 1 to 18 hours.

The novel dihydropyridine derivative (I) thus prepared can be recovered by optional means of separation and purification, for example, concentration, extraction, chromatography, reprecipitation and recrystallization, to collect a product in desired purity. Further, since the dihydropyridine derivative (I) has a basic group, it can also be converted to an acid addition salt by a conventional method. Such acid addition salts are not particularly limited so long as they are pharmaceutically acceptable and innoxious, and include, for example, inorganic acid salts (such as hydrochloride, hydrobromide, phosphate and sulfate) and organic acid salts (such as acetate, succinate, maleate, fumarate, malonate and tartrate).

The compounds having simultaneously a hydrogen atom for $R_1$ and $R_2$ are not sufficient in their activity, and the preferable compounds of the invention are exemplified as follows:

(1) 2,6-Dimethyl-4-(3-nitro-2-pyridyl)-1,4-dihydropyridine-3,5-dicarboxylic acid 3-β-(N-benzyl-N-methylamino)ethyl ester 5-methyl ester.

(2) 2,6-Dimethyl-4-(4-bromo-2-pyridyl)-1,4-dihydropyridine-3,5-dicarboxylic acid 3-β-(N-benzyl-N-methylamino)ethyl ester 5-methyl ester.

(3) 2,6-Dimethyl-4-(4-cyano-2-pyridyl)-1,4-dihydropyridyne-3,5-dicarboxylic acid 3-β-(N-benzyl-N-methylamino)ethyl ester 5-methyl ester.

(4) 2,6-Dimethyl-4-(4-trifluoromethyl-2-pyridyl)-1,4-dihydropyridine-3,5-dicarboxylic acid 3-β-(N-benzyl-N-methylamino)ethyl ester 5-methyl ester.

(5) 2,6-Dimethyl-4-(4-nitro-2-pyridyl)-1,4-dihydropyridine-3,5-dicarboxylic acid 3-β-(N-benzyl-N-methylamino)ethyl ester 5-methyl ester.

(6) 2,6-Dimethyl-4-(6-bromo-2-pyridyl)-1,4-dihydropyridine-3,5-dicarboxylic acid 3-β-(N-benzyl-N-methylamino)ethyl ester 5-methyl ester.

(7) 2,6-Dimethyl-4-(6-chloro-2-pyridyl)-1,4-dihydropyridine-3,5-dicarboxylic acid 3-β-(N-benzyl-N-methylamino)ethyl ester 5-methyl ester.

(8) 2,6-Dimethyl-4-(6-cyano-2-pyridyl)-1,4-dihydropyridine-3,5-dicarboxylic acid 3-β-(N-benzyl-N-methylamino)ethyl ester 5-methyl ester.

(9) 2,6-Dimethyl-4-(6-trifluoromethyl-2-pyridyl)-1,4-dihydropyridine-3,5-dicarboxylic acid 3-β-(N-benzyl-N-methylamino)ethyl ester 5-methyl ester.

(10) 2,6-Dimethyl-4-(6-nitro-2-pyridyl)-1,4-dihydropyridine-3,5-dicarboxylic acid 3-β-(N-benzyl-N-methylamino)ethyl ester 5-methyl ester.

(11) 2,6-Dimethyl-4-(2-bromo-3-pyridyl)-1,4-dihydropyridine-3,5-dicarboxylic acid 3-β-(N-benzyl-N-methylamino)ethyl ester.

(12) 2,6-Dimethyl-4-(2-cyano-3-pyridyl)-1,4-dihydropyridine-3,5-dicarboxylic acid 3-β-(N-benzyl-N-methylamino)ethyl ester 5-methyl ester.

(13) 2,6-Dimethyl-4-(2-trifluoromethyl-3-pyridyl)-1,4-dihydropyridine-3,5-dicarboxylic acid 3-β-(benzyl-N-methylamino)ethyl ester 5-methyl ester.

(14) 2,6-Dimethyl-4-(5-bromo-3-pyridyl)-1,4-dihydropyridine-3,5-dicarboxylic acid 3-β-(N-benzyl-N-methylamino)ethyl ester 5-methyl ester.

(15) 2,6-Dimethyl-4-(6-cyano-3-pyridyl)-1,4-dihydropyridine-3,5-dicarboxylic acid 3-β-(N-benzyl-N-methylamino)ethyl ester 5-methyl ester.

(16) 2,6-Dimethyl-4-(2-fluoro-4-pyridyl)-1,4-dihydropyridine-3,5-dicarboxylic acid 3-β-(N-benzyl-N-methylamino)ethyl ester 5-methyl ester.

(17) 2,6-Dimethyl-4-(5-trifluoromethyl-3-pyridyl)-1,4-dihydropyridine-3,5-dicarboxylic acid 3-β-(N-benzyl-N-methylamino)ethyl ester 5-methyl ester.

(18) 2,6-Dimethyl-4-(5-nitro-3-pyridyl)-1,4-dihydropyridine-3,5-dicarboxylic acid 3-β-(N-benzyl-N-methylamino)ethyl ester 5-methyl ester.

(19) 2,6-Dimethyl-4-(2-cyano-4-pyridyl)-1,4-dihydropyridine-3,5-dicarboxylic acid 3-β-(N-benzyl-N-methylamino)ethyl ester 5-methyl ester.

(20) 2,6-Dimethyl-4-(3-trifluoromethyl-2-pyridyl)-1,4-dihydropyridine-3,5-dicarboxylic acid 3-β-(N-benzyl-N-methylamino)ethyl ester 5-methyl ester.

The dihydropyridine derivative (I) and its innoxious salt according to this invention are of low toxicity, exert a strong and long-lasting blood pressure depressing action, peripheral blood vessel vasodilating action, coronary artery vasodilating action and celebral blood vessel vasodilating action on mammals such as mice, rats, rabbits, dogs, cats, and humans, and are useful as, for example, a preventive or curative agent for diseases of circulatory systems in humans, for example, hypertension, ischemic cardiac diseases (e.g. angina pectoris and myocardial infarction), and celebral and peripheral circulatory disorders (e.g. celebral infarction and transient celebral ischemic attack).

Particularly, they are excellent in both the intensity and/or the duration of their pharmacological effect as compared with dihydropyridine derivatives of prior art (for example Nifedipine and Nicardipine) and hence, when used as a preventive or curative agent for hypertension for example, can give a stable depression effect at a less number of times of administration (1 to 2 times per day).

When the dihydropyridine derivative (I) or its innoxious salt are used as the above-mentioned medicaments, they can be mixed with such pharmaceutically necessary ingredients as appropriate, pharmaceutically compatible carriers, additives, and diluents and made up into pharmaceutical compositions in the form of powders, granules, tablets, capsules, and injections, to be administered orally or parenterally.

The above-mentioned pharmaceutical preparations contain an effective amount of the dihydropyridine derivative (I) incorporated therein. The dosage varies depending upon the route of administration, the conditions, weight or age of patients, and other factors. In oral administration to adult hypertension patients for example, it is preferably administered at a dose of 0.05 to 20 mg/kg body weight/day, more preferably 0.1 to 4 mg/kg body weight/day, divided in 1 to several times per day.

The results of pharmacological tests conducted to show the effectiveness of the dihydropyridine derivative (I) and its innoxious salt of this invention are described below.

The results ($LD_{50}$) of acute toxicity test of the present Ca-antagonist (P.O.) in mice are 650°–950 mg/kg.

Blood pressure depression effect

Test 1

Male, spontaneously hypertension-developing rats of ages of 10 to 11 weeks (in groups of 3 to 5 animals) were used in the test. For blood pressure determination, systolic pressure was measured without anesthesia by an indirect tail-cuff method using a sphygmomanometer (PE-300, Narco Bio-System).

The compound to be tested was orally administered (at a dose of 25 mg/kg in terms of the active compound) as a 10% HCO-60 (polyoxyethylene hardened castor oil) suspension. Blood pressure was determined 1, 4 and 7 hours after the administration. Table 1 shows the respective average value of the blood pressure (in mmHg).

TABLE 1

| Compound Example | Systolic blood pressure (mmHg) | | | |
|---|---|---|---|---|
| | Before administration | After 1 hr | After 4 hrs | After 7 hrs |
| 1 | 193 | 115 | 137 | 148 |
| 3 | 198 | 126 | 143 | 161 |
| 5 | 195 | 156 | 135 | 140 |
| 6 | 190 | 139 | 145 | 145 |

Further, the blood pressure depression effect of the fumarate of the compound obtained in Example 28 described later was examined in the same manner as described above. The result obtained showed that the maximum depression value (%) of blood pressure from the value (100%) before administration was 67%, and the time required for 50% recovery from maximum depression value (%) of blood pressure was 16.2 hours.

Test 2

The above Test 1 was repeated with respect to a various compounds of the invention as well as Nicardipine and Nifedipine, including the compounds in Table 1, provided that the time after the administration was prolonged till 24 hours, and the blood pressure lowering maximum and the duration until the pressure recovered to 50% from the maximum depression value (%) of blood pressure were measured.

The results are shown as in Table 2, the changes of blood pressure being expressed as percent based on that before administration.

TABLE 2

| Compound No. | Before admini- stration | Depression value (%) of blood pressure | | | | | Duration 50% recovery (h) |
|---|---|---|---|---|---|---|---|
| | | 1h | 2h | 4h | 7h | 24h | Max | |
| Nic | 100 | 62 | 68 | 76 | 81 | 96 | 62 | 7.0 |
| Nif | 100 | 72 | 73 | 77 | 70 | 90 | 70 | 19.4 |
| (1) | 100 | 65 | 68 | 76 | 81 | 96 | 65 | 8.7 |
| (2) | 100 | 70 | 76 | 75 | 92 | 102 | 70 | 5.8 |
| (3) | 100 | 61 | 66 | 74 | 82 | 95 | 61 | 7.0 |
| (5) | 100 | 67 | 82 | 93 | 90 | 104 | 67 | 2.3 |
| (6) | 100 | 63 | 72 | 86 | 83 | 99 | 63 | 3.5 |
| (7) | 100 | 83 | 84 | 87 | 93 | 101 | 83 | 6.0 |
| (8) | 100 | 69 | 74 | 84 | 88 | 98 | 69 | 4.4 |
| (9) | 100 | 85 | 92 | 91 | 104 | 119 | 85 | 4.6 |
| (10) | 100 | 99 | 95 | 107 | 110 | 120 | 95 | 2.4 |
| (11) | 100 | 83 | 82 | 87 | 91 | 97 | 82 | 6.7 |
| (12) | 100 | 66 | 71 | 76 | 88 | 98 | 66 | 5.6 |
| (13) | 100 | 73 | 67 | 67 | 71 | 94 | 67 | 16.2 |
| (14) | 100 | 83 | 91 | 90 | 90 | 101 | 83 | 9.3 |
| (15) | 100 | 88 | 90 | 83 | 89 | 95 | 83 | 15.1 |
| (16) | 100 | 92 | 94 | 95 | 98 | 96 | 92 | 5.5 |
| (17) | 100 | 91 | 92 | 95 | 98 | 105 | 91 | 4.2 |
| (18) | 100 | 90 | 86 | 95 | 96 | 96 | 86 | 3.7 |
| (19) | 100 | 75 | 94 | 100 | 98 | 99 | 75 | 1.7 |

This invention will be explained in more detail below with reference to Examples.

EXAMPLE 1

(1)

2,6-Dimethyl-4-(6-cyano-2-pyridyl)-1,4-dihydropyridine-3,5-dicarboxylic acid 3-β-chloroethyl ester 5-methyl ester 6-Cyano-2-pyridine aldehyde (1.613 g, 12.2 mmol), chloroethyl acetoacetate (2.009 g, 12.2 mmol) and methyl 3-aminocrotonate (1.364 g, 12.2 mmol) were dissolved in 16 ml of isopropanol, and the solution was stirred at 35° to 40° C. under a nitrogen gas stream for 14 hours. The reaction solvent was distilled off under reduced pressure, and the residue was purified by column chromatography [silica gel; ethyl acetate-n-hexane (5:6)]. The crude product thus obtained was recrystallized from isopropyl ether-methanol to obtain 1.546 g (34% yield) of the above-captioned compound.

IR $\nu_{max}^{KBr}$ cm$^{-1}$: 2225(CN), 1695(C=O); 1680(C=O)

NMR δ CDCl$_3$:

7.7–7.3 (4H, NH and 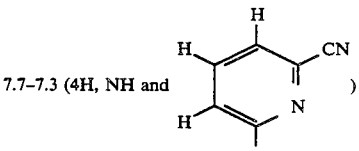 )

5.19 (1H, s, C$_4$—H)

4.27 (2H, t, J=6Hz, —CO$_2$CH$_2$CH$_2$Cl)

3.60 (3H, s, —CO$_2$CH$_3$)

3.60 (2H, t, J=6Hz, —CO$_2$CH$_2$CH$_2$Cl)

2.30 (6H, s, C$_2$— and C$_6$—CH$_3$)

(2)

2,6-Dimethyl-4-(6-cyano-2-pyridyl)-1,4-dihydropyridine-3,5-dicarboxylic acid 3-β-(N-benzyl-N-methylamino)ethyl ester 5-methyl ester.

The chloroethyl ester compound (1.546 g, 4.11 mmol) obtained in (1) and N-methyl-N-benzylamine (1.047 g, 8.64 mmol) were dissolved in 12 ml of N,N-dimethylformamide, and the solution was stirred at 100° to 105° C. under a nitrogen gas stream for 11.5 hours. The reaction solvent was distilled off under reduced pressure. The resulting residue was mixed with water and extracted with diethyl ether. The diethyl ether layer was washed with water, dried, and then the solvent was distilled off under reduced pressure. The residue was purified by column chromatography [silica gel; ethyl acetate-n-hexane (3:1)]. Thus, 449 mg (29% yield) of the starting material was recovered as the first fraction, and then 929 mg of the crude objective compound was obtained as the second fraction. The crude product was further purified by column chromatography [silica gel; chloroform-methanol (96:4)] to obtain 882 mg (47% yield) of the objective compound.

IR $\nu_{max}^{CHCl_3}$ cm$^{-1}$: 2225(CN), 1635(C=O×2)

NMR δ CDCl$_3$:

7.65–7.4 (3H, 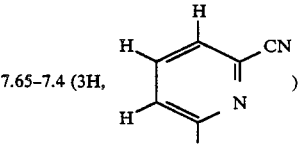 )

7.25 (5H, s, Ar—H)

6.92 (1H, s, \NH/)

5.22 (1H, s, C$_4$—H)

4.14 (2H, t, J=6Hz, —CO$_2$CH$_2$CH$_2$N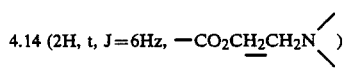)

3.60 (3H, s, —CO$_2$CH$_3$)

3.49 (2H, s, —N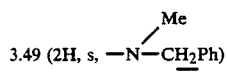—CH$_2$Ph)

2.60 (2H, t, J=6Hz, —CO$_2$CH$_2$CH$_2$N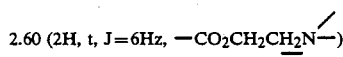—)

2.29 (6H, s, C$_2$— and C$_6$—CH$_3$)

2.18 (3H, s, 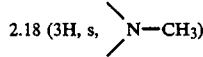N—CH$_3$)

EXAMPLE 2

The objective compound obtained in Example 1 (858 mg, 1.86 mmol) and fumaric acid (216 mg, 1.86 mmol) were dissolved in 25 ml of ethanol, and the solution was stirred at room temperature for 70 minutes. The reaction solvent was distilled off under reduced pressure to obtain 1.07 g of the fumaric acid salt of the compound.

IR $\nu_{max}^{KBr}$ cm$^{-1}$: 3300(COOH), 2200(CN), 1690(C=O×4)

NMR δ DMSO-d$_6$ + CDCl$_3$:

8.69 (1H, s, 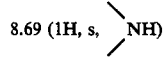NH)

7.7-7.45 (3H, 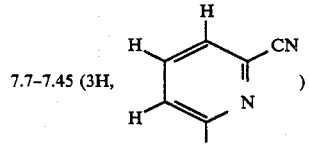)

7.22 (5H, s, Ar—H)

6.65 (2H, s, 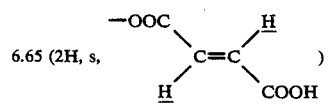)

5.12 (1H, s, C$_4$—H)

4.14 (2H, t, J=6Hz, —CO$_2$CH$_2$CH$_2$N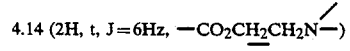—)

3.56 (5H, s, —CO$_2$CH$_3$ and —N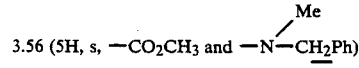—CH$_2$Ph)

2.67 (2H, t, J=6Hz, —CO$_2$CH$_2$CH$_2$N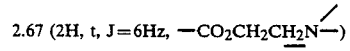—)

2.28 (6H, s, C$_2$— and C$_6$—CH$_3$)

2.21 (3H, s, —N—CH$_3$)

EXAMPLE 3

(1)
2,6-Dimethyl-4-(6-bromo-2-pyridyl)-1,4-dihydropyridine-3,5-dicarboxylic acid 3-β-chloroethyl ester 5-methyl ester A solution of 6-bromo-2-pyridine aldehyde (1.542 g, 8.29 mmol), chloroethyl acetoacetate (1.388 g, 8.43 mmol) and methyl 3-aminocrotonate (948 mg, 8.29 mmol) in 12 ml of isopropanol was stirred under a nitrogen gas stream, at 40° C. for 9 hours and at room temperature for 13 hours. The reaction solvent was distilled off under reduced pressure, and the residue was purified by column chromatography [silica gel; ethyl acetate-n-hexane (2:3)]. The crude product thus obtained was recrystallized from isopropyl ether-methanol to obtain 1.730 g (49% yield) of the above-captioned compound (m.p. 152° to 153°C.).

IR $\nu_{max}^{KBr}$ cm$^{-1}$: 1705(C=O), 1680(C=O)

NMR δ CDCl$_3$:

7.74 (1H, s, 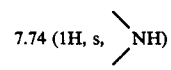NH)

7.5-7.15 (3H, 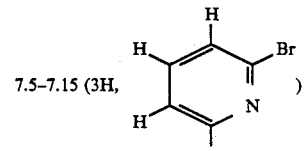)

5.25 (1H, s, C$_4$—H)

4.28 (2H, t, J=6Hz, —CO$_2$CH$_2$CH$_2$Cl)

3.60 (3H, s, —CO$_2$CH$_3$)

3.60 (2H, t, J=6Hz, —CO$_2$CH$_2$CH$_2$Cl)

2.32, 2.30 (respectively 3H, s, C$_2$— and C$_6$—CH$_3$)

(2)
2,6-Dimethyl-4-(6-bromo-2-pyridyl)-1,4-dihydropyridine-3,5-dicarboxylic acid 3-β-(N-benzyl-methylamino)ethyl ester 5-methyl ester The chloroethyl ester compound (1.509 g, 3.51 mmol) obtained in (1) and N-methyl-N-benzylamine (894 mg, 7.37 mmol) were dissolved in 11 ml of N,N-dimethylformamide, and the solution was stirred at 100° to 105° C. under a nitrogen gas stream for 15.5 hours. The reaction solvent was distilled off under reduced pressure. The residue was mixed with water and extracted with ethyl acetate. The ethyl acetate layer was washed with water, dried, and then the solvent was distilled off under reduced pressure. The residue was purified by column chromatography [silica gel; ethyl acetate-n-hexane (5:2)]. The crude product thus obtained was recrystallized from isopropyl ether-methanol to obtain 1.141 g (63% yield) of the objective compound. M.p.: 123.5° to 124.5° C.

IR $\nu_{max}^{KBr}$ cm$^{-1}$: 1695(C=O×2)

NMR δ CDCl$_3$:

7.66 (1H, s, 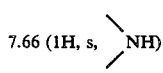NH)

7.45-7.2 (3H, 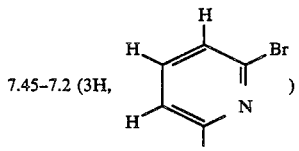)

7.28 (5H, s, Ar—H)

5.26 (1H, s, C$_4$—H)

4.17 (2H, t, J=6Hz, —CO$_2$CH$_2$CH$_2$N—)

3.60 (3H, s, CO$_2$CH$_3$)

3.50 (2H, s, —N—CH$_2$Ph)

2.61 (2H, t, J=6Hz, —CO$_2$CH$_2$CH$_2$N—)

2.30 (6H, s, C$_2$— and C$_6$—CH$_3$)

2.20 (3H, s, NCH$_3$)

EXAMPLE 4

The object compound (1.037 g, 2.02 mmol) obtained in Example 3 and fumaric acid (234 mg, 2.02 mmol) were dissolved in 24 ml of ethanol, and the solution was stirred at room temperature for 4 hours. The reaction solvent was distilled off under reduced pressure to obtain 1.2 g of the fumaric acid salt of the compound.

IR $\nu_{max}^{KBr}$ cm$^{-1}$: 3375(COOH), 1695(C=O×4)

NMR δ DMSO-d$_6$ + CDCl$_3$:

8.82 (1H, s, 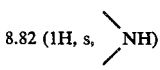NH)

7.5-7.05 (3H, 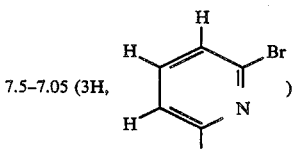)

7.27 (5H, s, Ar—H)

6.15 (2H, s, 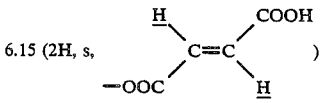)

5.08 (1H, s, C$_4$—H)

4.15 (2H, t, J=6Hz, —CO$_2$CH$_2$CH$_2$N—)

3.56 (5H, s, —CO$_2$CH$_3$ and —N—CH$_2$Ph with Me)

2.66 (2H, t, J=6Hz, —CO$_2$CH$_2$CH$_2$N—)

2.27 (6H, s, C$_2$— and C$_6$—CH$_3$)

2.19 (3H, s, NCH$_3$)

EXAMPLE 5

2,6-Dimethyl-4-(4-nitro-2-pyridyl)-1,4-dihydropyridine-3,5-dicarboxylic acid 3-β-(N-benzyl-N-methylamino)ethyl ester 5-methyl ester The same procedures as those in Example 1 were followed by using 4-nitro-2-pyridine aldehyde in place of 6-cyano-2-pyridine aldehyde to obtain the compound in 25% yield (m.p.: 163° C., methanol).

IR $\nu_{max}^{KBr}$ cm$^{-1}$: 3070, 2950, 1700, 1670, 1640, 1620, 1580

NMR δ CDCl$_3$:

8.6-7.6 (3H, 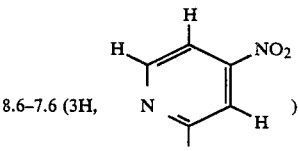)

7.2 (5H, s, Ar—H)

5.2 (1H, s, C$_4$—H)

4.1 (2H, t, J=6Hz, —CO$_2$CH$_2$CH$_2$—)

3.6 (3H, s, —CO$_2$CH$_3$)

3.5 (2H, s, —N(Me)—CH$_2$φ)

2.60 (2H, t, J=6Hz, —CO$_2$CH$_2$CH$_2$)

2.30 (6H, s, C$_2$— and C$_6$—CH$_3$)

2.2 (3H, s, N—CH$_3$)

EXAMPLE 6

2,6-Dimethyl-4-(2-trifluoromethyl-4-pyridyl)-1,4-dihydropyridine-3,5-dicarboxylic acid 3-β-(N-benzyl-N-methylamino)ethyl ester 5-methyl ester The same procedures were followed as those in Examples 3 by using 2-trifluoromethyl-4-pyridine aldehyde in place of 6-bromo-2-pyridine aldehyde to obtain the above objective compound in the form of oil (55% yield).

IR $\nu_{max}^{KBr}$ cm$^{-1}$: 3350, 2950, 2800, 1690(broad), 1460(broad)

H—NMR δ CDCl$_3$:

8.38–7.31 (3H, 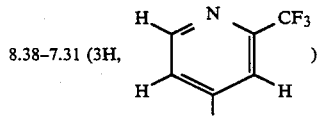 )

7.14 (5H, s, Ar—H)

6.43 (1H, s, HN )

5.06 (1H, s, C$_4$—H)

4.13 (2H, t, J=6Hz, —OC$\underline{H_2}$CH$_2$—)

3.60 (3H, s, —OCH$_3$)

3.47 (2H, s, —C$\underline{H_2}$φ)

2.63 (2H, t, J=6Hz, —OCH$_2$C$\underline{H_2}$—)

2.31 (6H, s, C$_2$— and C$_6$—CH$_3$)

2.17 (3H, s, \N—CH$_3$ /)

$^{19}$F—NMR φ CDCl$_3$: −67.5 (s)

EXAMPLES 7 TO 39

The compounds shown in Tables 3 to 6 were obtained in the same manner as in any one of Examples 1 to 6.

TABLE 3

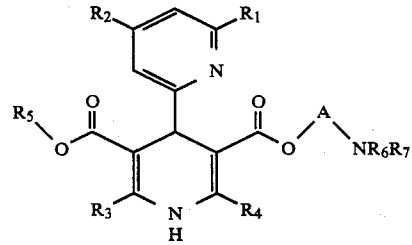

| Example | R$_1$ | R$_2$ | R$_3$ | R$_4$ | R$_5$ | A—NR$_6$R$_7$ | M.p. | Property |
|---|---|---|---|---|---|---|---|---|
| 7 | Cl | H | CH$_3$ | CH$_3$ | CH$_3$ | —CH$_2$CH$_2$N(CH$_3$)(CH$_2$φ) | 116–118° C. (Isopropyl ether) | Pale yellow powder |
| 8 | Br | " | " | " | " | " | 123.5–124.5° C. (Isopropyl ether) | Pale yellow powder |
| 9 | CN | " | " | " | " | " | — | Pale yellow oil |
| 10 | " | " | " | " | " | —CH$_2$CH$_2$N(tetrahydroquinolinyl) | — | Yellow oil |
| 11 | H | OMe | " | " | " | —CH$_2$CH$_2$N(CH$_3$)(CH$_2$φ) | 131–133° C. (Ethyl acetate) | Slightly yellow crystal |
| 12 | " | NO$_2$ | " | " | " | " | 157–159° C. (Methanol) | Slightly yellow crystal |
| 13 | CH$_3$ | H | " | " | " | " | — | Pale yellow oil |
| 14 | CF$_3$ | " | " | " | " | " | — | " |
| 15 | " | " | " | " | " | —CH$_2$CH$_2$N(imidazolyl) | — | " |

TABLE 3-continued

[Structure: pyridine ring with R1, R2 substituents connected to a dihydropyridine core with R3, R4, R5 substituents and an ester linkage to A—NR6R7]

| Example | R1 | R2 | R3 | R4 | R5 | A—NR6R7 | M.p. | Property |
|---|---|---|---|---|---|---|---|---|
| 16 | H | NO2 | " | " | " | —CH2CH2N(tetrahydroisoquinoline) | — | Pale yellow oil |
| 17 | CN | " | " | " | " | —CH2CH2N(CH3)(CH2φ) | 163° C. (Methanol) | Pale yellow crystal |
| 18 | H | CF3 | " | " | " | " | — | Pale yellow powder |
| 18 fumarate | " | " | " | " | " | " | — | Pale yellow powder |
| 19 | NO2 | H | " | " | " | " | — | Yellow oil |
| 19 fumarate | " | " | " | " | " | " | — | " |
| 20 | H | Br | " | " | " | " | — | Pale yellow powder |
| 20 fumarate | " | " | " | " | " | " | — | Pale yellow powder |
| 21 | " | CN | " | " | " | " | 176–177° C. (Isopropyl ether-methanol) | Pale yellow powder |
| 21 fumarate | " | " | " | " | " | " | — | Pale yellow powder |

TABLE 4

[Structure: pyridine ring with R2, (R'2), R1 substituents connected to a dihydropyridine with R3, R4, R5 and ester linkage to A—NR6R7]

| Example | R1 | R2(R'2) | R3 | R4 | R5 | A—NR6R7 | M.p. | Property |
|---|---|---|---|---|---|---|---|---|
| 22 | H | Br (R'2) | CH3 | CH3 | CH3 | —CH2CH2N(CH3)(CH2φ) | — | Pale yellow oil |
| 23 | " | CN | " | " | " | " | — | " |
| 24 | Br | H | " | " | " | " | 149–151° C. (Isopropyl ether) | Pale yellow powder |
| 25 | CN | " | " | " | " | " | 169–170.5° C. (Isopropyl ether) | " |
| 26 | H | NO2 (R'2) | " | " | " | " | 139–141.5° C. (Ethyl acetate) | Yellow powder |
| 27 | F | H | " | " | " | " | 79–82° C. (Isopropyl ether) | Pale yellow powder |
| 28 | CF3 | " | " | " | " | " | — | " |
| 28 fumarate | " | " | " | " | " | " | — | " |

TABLE 4-continued

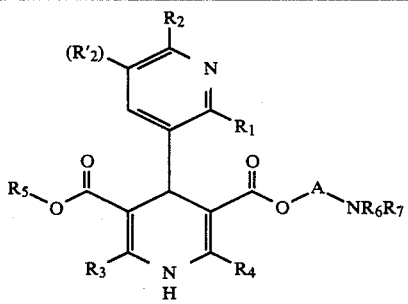

| Example | R₁ | R₂(R'₂) | R₃ | R₄ | R₅ | A—NR₆R₇ | M.p. | Property |
|---|---|---|---|---|---|---|---|---|
| 29 | CN | " | " | " | " | —CH₂CH₂N(benzimidazolyl) | — | Pale yellow oil |
| 30 | CF₃ | " | " | " | " | —CH₂CH₂N(tetrahydroquinolinyl) | — | " |
| 31 | H | CF₃ (R'₂) | " | " | " | —CH₂CH₂N(CH₃)(CH₂φ) | — | " |
| 31 fumarate | " | " | " | " | " | " | — | Pale yellow powder |

TABLE 5

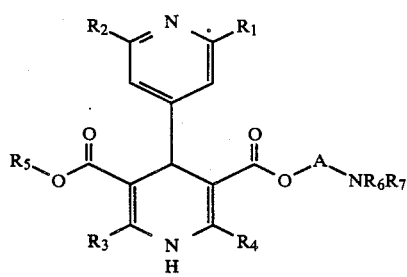

| Example | R₁ | R₂ | R₃ | R₄ | R₅ | A—NR₆R₇ | M.p. | Property |
|---|---|---|---|---|---|---|---|---|
| 32 | Br | H | CH₃ | CH₃ | CH₃ | —CH₂CH₂N(CH₃)(CH₂φ) | | Pale yellow oil |
| 33 | CN | " | " | " | " | " | (IR. 2225 cm⁻¹) | " |
| 34 | F | " | " | " | " | " | | " |
| 35 | CF₃ | " | " | " | " | " | | " |
| 36 | " | " | " | " | " | —CH₂CH₂N(tetrahydroquinolinyl) | | " |

TABLE 5-continued

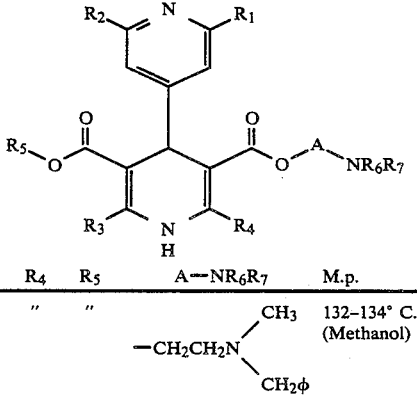

| Example | R₁ | R₂ | R₃ | R₄ | R₅ | A—NR₆R₇ | M.p. | Property |
|---|---|---|---|---|---|---|---|---|
| 37 | CN | CN | " | " | " | —CH₂CH₂N(CH₃)(CH₂φ) | 132–134° C. (Methanol) | Pale yellow powder |

TABLE 6

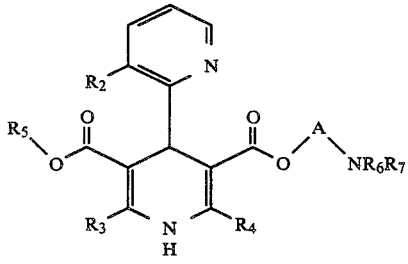

| Example | R₁ | R₂ | R₄ | R₅ | A—NR₆R₇ | Property |
|---|---|---|---|---|---|---|
| 38 | CF₃ | CH₃ | CH₃ | CH₃ | —CH₂CH₂N(CH₃)(CH₂φ) | Pale yellow powder |
| 38 fumarate | " | " | " | " | " | " |

TABLE 6-continued

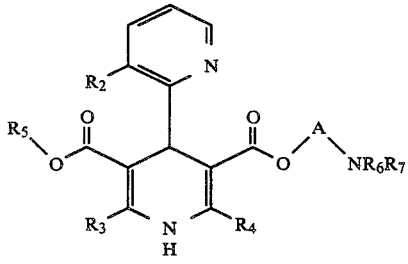

| Example | R₁ | R₂ | R₄ | R₅ | A—NR₆R₇ | Property |
|---|---|---|---|---|---|---|
| 39 | NO₂ | " | " | " | " | Yellow oil |
| 39 fumarate | " | " | " | " | " | Yellow oil |

Some of the compounds obtained in Examples 7 to 39 can be identified by means of nuclear magnetic resonance and others, as shown in Table 7.

TABLE 7

| Example No. | H—NMR δ CDCl₃ | Other properties |
|---|---|---|
| 14 | 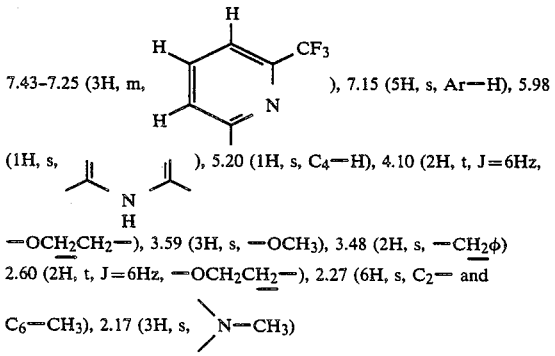 7.43–7.25 (3H, m, [pyridyl-CF₃]), 7.15 (5H, s, Ar—H), 5.98 (1H, s, [NH]), 5.20 (1H, s, C₄—H), 4.10 (2H, t, J=6Hz, —OCH₂CH₂—), 3.59 (3H, s, —OCH₃), 3.48 (2H, s, —CH₂φ) 2.60 (2H, t, J=6Hz, —OCH₂CH₂—), 2.27 (6H, s, C₂— and C₆—CH₃), 2.17 (3H, s, N—CH₃) | ¹⁹F—NMR φ (CDCl₃): −67.8 ppm |

TABLE 7-continued

| Example No. | H—NMR δ CDCl$_3$ | Other properties |
|---|---|---|
| 14 fumarate | 8.99 (1H, s, [pyridine with CF$_3$ structure]), 7.87 (1H, dd, J=7.56, 7.84Hz, [pyridine with CF$_3$]), 7.60 (1H, d, J=7.56Hz, [pyridine with CF$_3$]), 7.45 (1H, d, J=7.84Hz, [pyridine with CF$_3$]), 7.27 (5H, s, Ar—H), 6.63 (2H, s, [fumarate HC=CH structure with CO$_2$H]), 5.17 (1H, s, C$_4$—H), 4.14 (2H, t, J=5.66Hz, —OC$\underline{H_2}$CH$_2$—), 3.55 (3H, s, —OCH$_3$), 3.55 (2H, s, —C$\underline{H_2}$φ), 2.63 (2H, t, J=5.66Hz, —OCH$_2$C$\underline{H_2}$—), 2.27 (6H, s, C$_2$— and C$_6$—CH$_3$), 2.15 (3H, s, \N—CH$_3$/) (DMSO-d$_6$ was used) | $^{19}$F—NMR φ (DMSO-d$_6$): −65.9 ppm IR ν$_{max}^{KBr}$ cm$^{-1}$: 1700(C=O) |
| 18 | 8.63 (1H, d, J=5Hz, [pyridine with F$_3$C]), 7.60 (1H, s, [pyridine with F$_3$C]), 7.60 (1H, s, [structure]) 7.30 (1H, d, J=5Hz, [pyridine with F$_3$C]), 7.23 (5H, s, Ar—H), 5.27 (1H, s, C$_4$—H), 4.13 (2H, t, J=6.2Hz, —OC$\underline{H_2}$CH$_2$—), 3.60 (3H, s, —OCH$_3$), 3.48 (2H, s, —C$\underline{H_2}$φ), 2.60 (2H, t, J=6.2Hz, —OCH$_2$C$\underline{H_2}$—), 2.25 (6H, s, C$_2$— and C$_6$—CH$_3$), 2.17 (3H, s, \N—CH$_3$/) | $^{19}$F—NMR φ (CDCl$_3$): −64.8 ppm IR ν$_{max}^{KBr}$ cm$^{-1}$: 1700(C=O) |
| 18 fumarate | 8.72 (1H, s, [structure]), 8.64 (1H, d, [pyridine with F$_3$C]), 7.40 (1H, s, [pyridine with F$_3$C]), 7.20–7.40 (1H, overlap, [pyridine with F$_3$C]), 7.20 (5H, s, Ar—H), 6.62 (2H, s, [fumarate HC=CH structure with CO$_2$H]) 5.13 (1H, s, C$_4$—H), 4.10 (2H, t, —OC$\underline{H_2}$CH$_2$—), 3.52 (3H, s, —OCH$_3$), 3.48 (2H, s, —C$\underline{H_2}$φ), 2.58 (2H, t, —OCH$_2$C$\underline{H_2}$—), 2.25 (6H, s, C$_2$— and C$_6$—CH$_3$), 2.13 (3H, s, \N=CH$_3$/) (CDCl$_3$: DMSO-d$_6$ = 1:2 was used) | $^{19}$F—NMR φ (CDCl$_3$, DMSO-d$_6$): −63.3 ppm IR ν$_{max}^{KBr}$ cm$^{-1}$: 1710(C=O) |

TABLE 7-continued

| Example No. | H—NMR δ CDCl$_3$ | Other properties |
|---|---|---|
| 19 | 7.95–7.55 (3H, [3-nitropyridyl ring with H positions]), 7.19 (5H, s, Ar—H), 6.33 (1H, s, [enamine =CH–NH–CH=]), 5.25 (1H, s, C$_4$—H), 4.14 (2H, t, J=6Hz, —OC$\underline{H_2}$CH$_2$—), 3.60 (3H, s, —OCH$_3$), 3.47 (2H, s, —C$\underline{H_2}$φ), 2.60 (2H, t, J=6Hz, —OCH$_2$C$\underline{H_2}$—), 2.30 (6H, s, C$_2$— and C$_6$—CH$_3$), 2.18 (3H, s, >N—CH$_3$) | IR $\nu_{max}^{CHCl_3}$ cm$^{-1}$: 1690(C=O), 1540(NO$_2$) 1355(NO$_2$) |
| 19 fumarate | 8.84 (1H, s, [enamine]), 8.15–7.55 (3H, [nitropyridyl]), 7.24 (5H, s, Ar—H), 6.64 (2H, s, fumarate HC=CH), 5.20 (1H, s, C$_4$—H), 4.16 (2H, t, J=6Hz, —OC$\underline{H_2}$CH$_2$—), 3.57 (3H, s, —OCH$_3$), 3.54 (2H, s, —C$\underline{H_2}$φ), 2.66 (2H, t, J=6Hz, —OCH$_2$C$\underline{H_2}$—), 2.30 (6H, s, C$_2$— and C$_6$—CH$_3$), 2.19 (3H, s, >N—CH$_3$) (CDCl$_3$: DMSO—d$_6$ = 1.5:2 was used) | IR $\nu_{max}^{KBr}$ cm$^{-1}$: 3400(COO$\underline{H}$), 1690(C=O), 1540(NO$_2$), 1355(NO$_2$). |
| 20 | 8.3–8.05 (2H, [4-bromopyridyl H] and [enamine]), 7.6–7.5 (1H, [bromopyridyl]), 7.3–7.1 (6H, [bromopyridyl] and Ar—H), 5.11 (1H, s, C$_4$—H), 4.14 (2H, t, J=6Hz, —OC$\underline{H_2}$CH$_2$—), 3.61 (3H, s, —OCH$_3$), 3.49 (2H, s, —C$\underline{H_2}$φ), 2.62 (2H, t, J=6Hz, —OCH$_2$C$\underline{H_2}$—), 2.22 (9H, s, C$_2$—, C$_6$—CH$_3$ and >N—CH$_3$) | IR $\nu_{max}^{KBr}$ cm$^{-1}$: 1700(C=O), 1675(C=O) |

TABLE 7-continued

| Example No. | H—NMR δ CDCl₃ | Other properties |
|---|---|---|
| 20 fumarate | 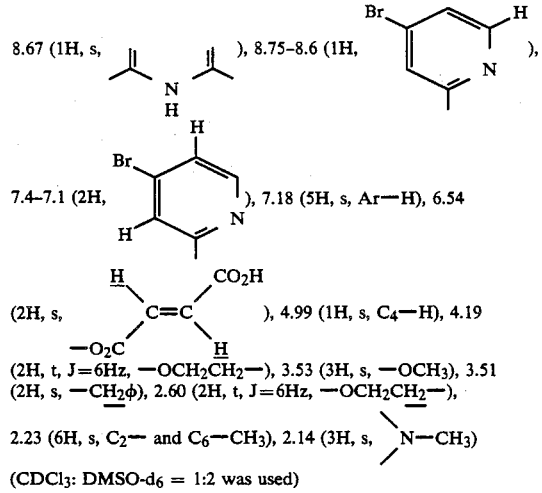 8.67 (1H, s, [isopropylidene-NH-isopropylidene]), 8.75–8.6 (1H, [4-Br-pyridyl H]), 7.4–7.1 (2H, [4-Br-pyridyl H]), 7.18 (5H, s, Ar—H), 6.54 (2H, s, [fumarate HC=CH]), 4.99 (1H, s, C₄—H), 4.19 (2H, t, J=6Hz, —OCH₂CH₂—), 3.53 (3H, s, —OCH₃), 3.51 (2H, s, —CH₂φ), 2.60 (2H, t, J=6Hz, —OCH₂CH₂—), 2.23 (6H, s, C₂— and C₆—CH₃), 2.14 (3H, s, N—CH₃)<br>(CDCl₃: DMSO-d₆ = 1:2 was used) | IR $\nu_{max}^{KBr}$ cm$^{-1}$: 3400(COOH), 1695(C=O) |
| 21 | 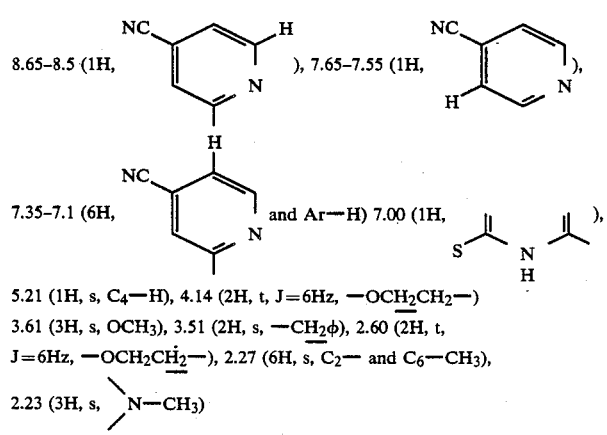 8.65–8.5 (1H, [4-CN-pyridyl H]), 7.65–7.55 (1H, [4-CN-pyridyl H]), 7.35–7.1 (6H, [4-CN-pyridyl and Ar—H]) 7.00 (1H, [thioamide NH]), 5.21 (1H, s, C₄—H), 4.14 (2H, t, J=6Hz, —OCH₂CH₂—) 3.61 (3H, s, OCH₃), 3.51 (2H, s, —CH₂φ), 2.60 (2H, t, J=6Hz, —OCH₂CH₂—), 2.27 (6H, s, C₂— and C₆—CH₃), 2.23 (3H, s, N—CH₃) | IR $\nu_{max}^{KBr}$ cm$^{-1}$: 2250(CN), 1710(C=O), 1665(C=O) |
| 21 fumarate | 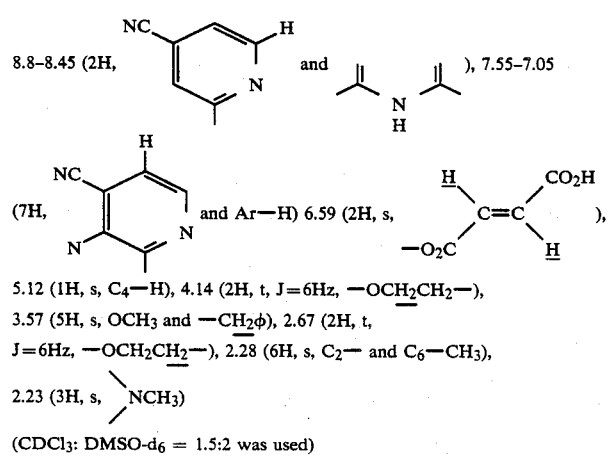 8.8–8.45 (2H, [4-CN-pyridyl H and isopropylidene-NH-isopropylidene]), 7.55–7.05 (7H, [4-CN-pyridyl and Ar—H]) 6.59 (2H, s, [fumarate HC=CH]), 5.12 (1H, s, C₄—H), 4.14 (2H, t, J=6Hz, —OCH₂CH₂—), 3.57 (5H, s, OCH₃ and —CH₂φ), 2.67 (2H, t, J=6Hz, —OCH₂CH₂—), 2.28 (6H, s, C₂— and C₆—CH₃), 2.23 (3H, s, NCH₃)<br>(CDCl₃: DMSO-d₆ = 1.5:2 was used) | IR $\nu_{max}^{KBr}$ cm$^{-1}$: 3400(COOH), 2250(CN), 1695(C=O). |

TABLE 7-continued

| Example No. | H—NMR δ CDCl$_3$ | Other properties |
|---|---|---|
| 27 | 7.4-7.9 (2H, m, [2-fluoro-3-methylpyridin-5-yl fragment]), 7.1 (5H, s, Ar—H), 6.8-7.0 (1H, m, [2-fluoro-3-methylpyridin-5-yl fragment]), 6.1 (1H, s, [CH=C(NH)CH= enamine fragment]), 5.1 (1H, s, C$_4$—H), 4.1 (2H, t, J=6Hz, —OCH$_2$CH$_2$—), 3.5 (3H, s, —OCH$_3$), 3.4 (2H, s, —CH$_2$φ), 2.6 (2H, t, J=6Hz, —OCH$_2$CH$_2$—), 2.3 (6H, s, C$_2$— and C$_6$—CH$_3$), 2.2 (3H, s, \N—CH$_3$) | $^{19}$F—NMR φ (DMSO-d$_6$, CDCl$_3$): −72 ppm<br>IR ν$_{max}^{KBr}$ cm$^{-1}$<br>1700(C=O) |
| 27 fumarate | 8.5 (1H, s, [enamine NH fragment]), 7.75-7.90 (1H, m, [pyridinyl fragment]), 7.47-7.75 (1H, m, [pyridinyl fragment]), 7.25 (5H, s, Ar—H), 6.87-7.20 (2H, m, [pyridinyl fragment] and —CO$_2$H), 6.63 (2H, s, [fumarate HC=CH fragment, H-C=C-CO$_2$H / O$_2$C-C=C-H]), 5.08 (1H, s, C$_4$—H), 4.10 (2H, t, J=5.5Hz, —OCH$_2$CH$_2$—), 3.50 (5H, s, —CH$_2$φ and —OCH$_3$), 2.67 (2H, t, J=5.5Hz, —OCH$_2$CH$_2$—), 2.27 (6H, s, C$_2$— and C$_6$—CH$_3$), 2.20 (3H, s, \N—CH$_3$)<br>(CDCl$_3$: DMSO-d$_6$ = 2:1 was used) | $^{19}$F—NMR φ (CFCl$_3$, DMSO-d$_6$): −72 ppm<br>IR ν$_{max}^{KBr}$ cm$^{-1}$<br>3200-3600(COOH)<br>1700(C=O), |
| 28 | 8.4 (1H, d, J=4.3Hz, [2-trifluoromethyl-3-methylpyridin-6-yl fragment]), 7.8 (1H, d, J=7.7Hz, [2-trifluoromethyl-3-methylpyridin-4-yl fragment]), 7.3 (1H, d, d, J=7.7Hz, 4.3Hz, [2-trifluoromethyl-3-methylpyridin-5-yl fragment]), 7.2 (5H, s, Ar—H), 5.9 (H, s, [enamine fragment]), 5.6 (1H, s, C$_4$—H), 4.1 (2H, t, J=6Hz, —OCH$_2$CH$_2$—), 3.5 (3H, s, —OCH$_3$), 3.4 (2H, s, —CH$_2$φ), 2.6 (2H, t, J=6Hz, —OCH$_2$CH$_2$—), 2.3 (6H, s, C$_2$— and C$_6$—CH$_3$), 2.1 (3H, s, \N—CH$_3$) | $^{19}$F—NMR φ (CDCl$_3$): −61 ppm<br>IR ν$_{max}^{KBr}$ cm$^{-1}$:<br>1700(C=O) |

TABLE 7-continued

| Example No. | H—NMR δ CDCl₃ | Other properties |
|---|---|---|
| 28 fumarate | 8.9 (1H, s, 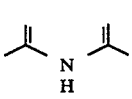), 8.4 (1H, d, 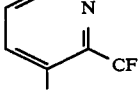), 7.9 (1H, d, 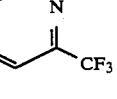), 7.5 (1H, d, d, 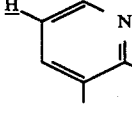), 7.2 (5H, s, Ar—H), 6.6 (2H, s, 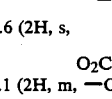), 5.4 (1H, s, C₄—H), 4.1 (2H, m, —OC$\underline{H_2}$CH₂—), 3.4 (5H, s, —C$\underline{H_2}$φ and —OCH₃), 2.5 (2H, t, —OCH₂C$\underline{H_2}$—), 2.2 (6H, s, C₂— and C₆—CH₃) 2.1 (3H, s, 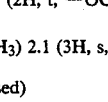) (DMSO-d₆ was used) | ¹⁹F—NMR φ (CDCl₃: DMSO-d₆) = 1:2.5: −61 ppm IR $\nu_{max}^{KBr}$ cm⁻¹: 1700(C=O) |
| 31 | 8.67, 8.60 (2H, overlapped, 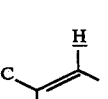), 7.77 (1H, m, 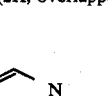), 7.20 (5H, s, Ar—H), 6.07 (1H, s, 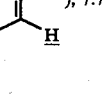), 5.07 (1H, s, C₄—H) 4.15 (2H, t, J=6Hz, —OC$\underline{H_2}$CH₂—), 3.60 (3H, s, —OCH₃), 3.48 (2H, s, —C$\underline{H_2}$φ), 2.59 (2H, t, J=6Hz, —OCH₂C$\underline{H_2}$—), 2.30 (6H, s, C₂— and C₆—CH₃), 2.17 (3H, s, 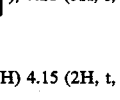) | ¹⁹F—NMR φ (CDCl₃): −62.5 ppm IR $\nu_{max}^{KBr}$ cm⁻¹: 1600-1720(C=O) |
| 31 fumarate | 9.07 (1H, s, 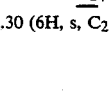), 8.70 (2H, s, ), 7.77 (1H, s, 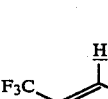), 7.23 (5H, s, Ar—H), 6.62 (2H, s, 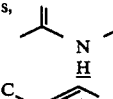), 4.98 (1H, s, C₄—H), 4.12 (2H, t, —OC$\underline{H_2}$CH₂—), 3.54 (5H, overlapped, —C$\underline{H_2}$φ and —OCH₃), 2.57 (2H, t, —OCH₂C$\underline{H_2}$—), 2.30 (6H, s, C₂— and C₆—CH₃), 2.13 (3H, s, 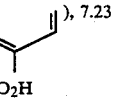) (DMSO-d₆ was used) | ¹⁹F—NMR φ (DMSO-d₆): −60.5 ppm IR $\nu_{max}^{KBr}$ cm⁻¹: 1700(C=O) |

TABLE 7-continued

| Example No. | H—NMR δ CDCl$_3$ | Other properties |
|---|---|---|
| 38 | 8.60 (1H, d, J=4.3Hz, 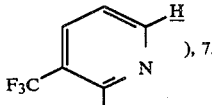), 7.75 (1H, d, J=4.7Hz, 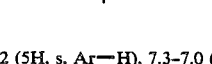), 7.2 (5H, s, Ar—H), 7.3-7.0 (1H, dd, overlapped with phenyl proton, 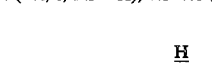), 6.78 (1H, s, ), 5.63 (1H, s, C$_4$—H), 3.80–4.40 (2H, m, —OCH$_2$CH$_2$—), 3.52 (3H, s, —OCH$_3$), 3.42 (2H, s, —CH$_2$φ), 2.53 (2H, t, J=6.5Hz, —OCH$_2$CH$_2$—), 2.22 (6H, s, C$_2$— and C$_6$—CH$_3$), 2.13 (3H, s, 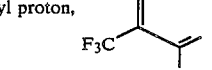N—CH$_3$) | $^{19}$F—NMR φ (CDCl$_3$): −56.5 ppm<br>IR $\nu_{max}^{KBr}$ cm$^{-1}$: 1720(C=O) |
| 38 fumarate | 8.63 (1H, d, 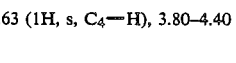), 8.40 (1H, s, 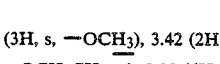), 7.78 (1H, d, 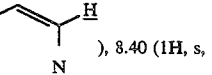), 7.20 (5H, s, Ar—H), 7.0-7.3 (1H, m, ), 6.70 (2H, s, 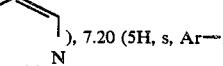), 5.57 (1H, s, C$_4$—H), 4.13 (2H, m, —OCH$_2$CH$_2$—), 3.50 (5H, s, —CH$_2$φ and —OCH$_3$), 2.60 (2H, d, —OCH$_2$CH$_2$—), 2.26 (6H, s, C$_2$— and C$_6$—CH$_3$), 2.17 (3H, s, N—CH$_3$)<br>(CDCl$_3$: DMSO-d$_6$ = 3.1 was used) | $^{19}$F—NMR φ (CDCl$_3$, DMSO-d$_6$): −56.0 ppm<br>IR $\nu_{max}^{KBr}$ cm$^{-1}$: 1700(C=O) |

TABLE 7-continued

| Example No. | H—NMR δ CDCl₃ | Other properties |
|---|---|---|
| 39 | 8.7-8.5 (1H, [pyridine-NO₂]), 8.1-7.85 (1H, [pyridine-NO₂]), 7.3-7.0 (1H, [pyridine-NO₂]), 7.17 (5H, s, Ar—H), 6.32 (1H, s, [dihydropyridine]), 5.90 (1H, s, C₄—H), 4.14 (2H, t, J=6Hz, —CO₂CH₂CH₂N=), 3.52 (3H, s, —CO₂CH₃), 3.41 (2H, s, —C$\underline{H_2}$φ), 2.57 (2H, t, J=6Hz, —CO₂CH₂C$\underline{H_2}$N=), 2.28 (6H, s, C₂— and C₆—CH₃), 2.13 (3H, s, $\diagdown$N—CH₃) | IR ν$_{max}^{CHCl_3}$ cm⁻¹: 1690(C=O), 1520(NO₂), 1355(NO₂) |
| 39 fumarate | 8.8-8.5 (2H, [pyridine-NO₂] and [dihydropyridine]), 8.2-7.95 (1H, [pyridine-NO₂]), 7.45-7.1 (1H, [pyridine-NO₂]), 7.20 (5H, s, Ar—H), 6.11 (2H, s, —O₂C—C=O(H)—CO₂H), 5.75 (1H, s, C₄—H), 4.08 (2H, t, J=6Hz, —CO₂CH₂CH₂N—), 3.45 (5H, s, —CO₂CH₃ and —C$\underline{H_2}$φ), 2.27, 2.25 (respectively 3H, s, C₂— and C₆—CH₃), 2.11 (3H, s, $\diagdown$N—CH₃) (CDCl₃: DMSO-d₆ = 1.5:2 was used) | IR ν$_{max}^{KBr}$ cm⁻¹: 3400(COO$\underline{H}$), 1685(C=O), 1530(NO₂), 1355(NO₂) |

Preparation Example

Any one of the present compound (interms of active compound: 10 mg
Magnesium stearate: 2 mg
Hydroxypropyl cellulose: 2 mg The above ingredients were mixed with starch to obtain 300 mg of a tablet preparation, according to a conventional tablet preparation method.

What is claimed is:

1. A dihydropyridine derivative of the formula

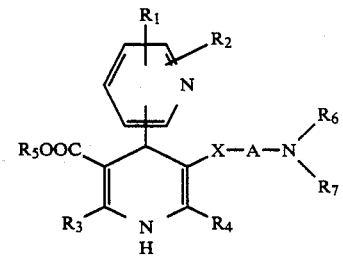

wherein $R_1$ and $R_2$ are the same or different from each other and each denotes hydrogen, nitro, cyano, halogen, $C_1$-$C_6$ alkyl, partially or fully fluorinated $C_1$-$C_6$ alkyl, $C_1$-$C_6$ alkoxy, partially or fully fluorinated $C_1$-$C_6$ alkoxy, $C_1$-$C_6$ alkylmercapto, $C_1$-$C_6$ alkylsulfinyl or $C_1$-$C_6$ alkylsulfonyl, provided that they cannot be hydrogen at the same time;

R$_3$, R$_4$ and

R$_5$ denote C$_1$-C$_6$ alkyl;

R$_6$ denotes hydrogen or C$_1$-C$_6$ alkyl;

R$_7$ denotes hydrogen, C$_1$-C$_6$ alkyl, phenyl C$_1$-C$_3$ alkyl, halogen-substituted phenyl C$_1$-C$_3$ alkyl wherein the halogen is selected from the group consisting of fluorine, chlorine, bromine and iodine as a substituent or R$_6$ and R$_7$ form jointly with the adjacent nitrogen atom 1,2,3-tetrahydroquinolinyl, 1,2,3-tetrahydroisoquinolinyl, or benzimidazolyl;

X denotes a group —COO—; and A denotes a C$_2$-C$_4$ alkylene group, or a pharmaceutically acceptable salt thereof.

2. A dihydropyridine derivative of claim 1, wherein the derivative has the formula,

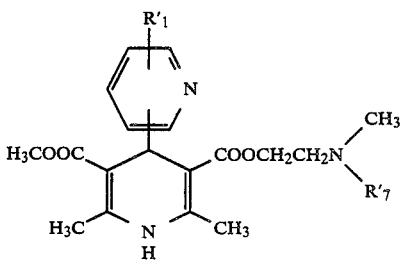

wherein R'$_1$ denotes methyl, chlorine, bromine, fluorine, trifluoromethyl, nitro, cyano or methoxy, R'$_7$ denotes benzyl; and the dihydropyridine links to the 2-, 3-, or 4-position of the pyridine.

3. A dihydropyridine derivative of claim 2, which is 2,6-dimethyl-4-(3-nitro-2-pyridyl)-1,4-dihydropyridine-3,5-dicarboxylic acid 3-β-(N-benzyl-N-methylamino)ethyl ester 5-methyl ester.

4. A dihydropyridine derivative of claim 2, which is 2,6-dimethyl-4-(4-bromo-2-pyridyl)-1,4-dihydropyridine-3,5-dicarboxylic acid 3-β-(N-benzyl-N-methylamino)ethyl ester 5-methyl ester.

5. A dihydropyridine derivative of claim 2, which is 2,6-dimethyl-4-(4-cyano-2-pyridyl)-1,4-dihydropyridine-3,5-dicarboxylic acid 3-β-(N-benzyl-N-methylamino)ethyl ester 5-methyl ester.

6. A dihydropyridine derivative of claim 2, which is 2,6-dimethyl-4-(6-cyano-2-pyridyl)-1,4-dihydropyridine-3,5-dicarboxylic acid 3-β-(N-benzyl-N-methylamino)ethyl ester 5-methyl ester.

7. A dihydropyridine derivative of claim 2, which is 2,6-dimethyl-4-(4-nitro-2-pyridyl)-1,4-dihydropyridine-3,5-dicarboxylic acid 3-β-(N-benzyl-N-methylamino)ethyl ester 5-methyl ester.

8. A dihydropyridine derivative of claim 2, which is 2,6-dimethyl-4-(6-bromo-2-pyridyl)-1,4-dihydropyridine-3,5-dicarboxylic acid 3-β-(N-benzyl-N-methylamino)ethyl ester 5-methyl ester.

9. A dihydropyridine derivative of claim 2, which is 2,6-dimethyl-4-(6-chloro-2-pyridyl)-1,4-dihydropyridine-3,5-dicarboxylic acid 3-β-(N-benzyl-N-methylamino)ethyl ester 5-methyl ester.

10. A dihydropyridine derivative of claim 2, which is 2,6-dimethyl-4-(6-trifluoromethyl-2-pyridyl)-1,4-dihydropyridine-3,5-dicarboxylic acid 3-β-(N-benzyl-N-methylamino)ethyl ester 5-methyl ester.

11. A dihydropyridine derivative of claim 2, which is 2,6-dimethyl-4-(4-trifluoromethyl-2-pyridyl)-1,4-dihydropyridine-3,5-dicarboxylic acid 3-β-(N-benzyl-N-methylamino)ethyl ester 5-methyl ester.

12. A dihydropyridine derivative of claim 2, which is 2,6-dimethyl-4-(2-bromo-3-pyridyl)-1,4-dihydropyridine-3,5-dicarboxylic acid 3-β-(N-benzyl-N-methylamino)ethyl ester 5-methyl ester.

13. A dihydropyridine derivative of claim 2, which is 2,6-dimethyl-4-(2-cyano-3-pyridyl)-1,4-dihydropyridine-3,5-dicarboxylic acid 3-β-(N-benzyl-N-methylamino)ethyl ester 5-methyl ester.

14. A dihydropyridine derivative of claim 2, which is 2,6-dimethyl-4-(2-trifluoromethyl-3-pyridyl)-1,4-dihydropyridine-3,5-dicarboxylic acid 3-β-(N-benzyl-N-methylamino)ethyl ester 5-methyl ester.

15. A dihydropyridine derivative of claim 2, which is 2,6-dimethyl-4-(5-bromo-3-pyridyl)-1,4-dihydropyridine-3,5-dicarboxylic acid 3-β-(N-benzyl-N-methylamino)ethyl ester 5-methyl ester.

16. A dihydropyridine derivative of claim 2, which is 2,6-dimethyl-4-(6-cyano-3-pyridyl)-1,4-dihydropyridine-3,5-dicarboxylic acid 3-β-(N-benzyl-N-methylamine)ethyl ester 5-methyl ester.

17. A dihydropyridine derivative of claim 2, which is 2,6-dimethyl-4-(6-nitro-2-pyridyl)-1,4-dihydropyridine-3,5-dicarboxylic acid 3-β-(N-benzyl-N-methylamino)ethyl ester 5-methyl ester.

18. A dihydropyridine derivative of claim 2, which is 2,6-dimethyl-4-(5-nitro-3-pyridyl)-1,4-dihydropyridine-3,5-dicarboxylic acid 3β-(N-benzyl-N-methylamino)ethyl ester 5-methyl ester.

19. A dihydropyridine derivative of claim 2, which is 2,6-dimethyl-4-(5-trifluoromethyl-3-pyridyl)-1,4-dihydropyridine-3,5-dicarboxylic acid 3-β-(N-benzyl-N-methylamino)ethyl ester 5-methyl ester.

20. A dihydropyridine derivative of claim 2, which is 2,6-dimethyl-4-(2-cyano-4-pyridyl)-1,4-dihydropyridine-3,5-dicarboxylic acid 3-β-(N-benzyl-N-methylamino)ethyl ester 5-methyl ester.

21. A dihydropyridine derivative of claim 2, which is 2,6-dimethyl-4-(3-trifluoromethyl-2-pyridyl)-1,4-dihydropyridine-3,5-dicarboxylic acid 3-β-(N-Benzyl-N-methylamino)ethyl ester 5-methyl ester.

22. A pharmaceutical composition useful for treating vascular disorders such as coronary artery disease, cerebral artery disease, hypertension and the like, which comprises an effective amount of the dihydropyridine derivative or a pharmaceutically acceptable salt thereof of claim 1, and a diluent.

23. A dihydropyridine derivative of claim 1, wherein the partially or fully fluorinated C$_1$-C$_6$ alkyl is CF$_3$—, CF$_3$CH$_2$— or (CF$_3$)$_2$CHCH$_2$—.

* * * * *